(12) United States Patent
Thompson

(10) Patent No.: US 6,398,725 B1
(45) Date of Patent: Jun. 4, 2002

(54) ENDOSCOPE HAVING ELEVATION AND AZIMUTH CONTROL OF CAMERA

(75) Inventor: Robert Lee Thompson, Dallas, TX (US)

(73) Assignee: Pinotage, LLC, Fayetville, AR (US)

( * ) Notice: Subject to any disclaimer, the term of this patent is extended or adjusted under 35 U.S.C. 154(b) by 0 days.

(21) Appl. No.: 09/382,496

(22) Filed: Aug. 25, 1999

Related U.S. Application Data (62) Division of application No. 09/065,116, filed on Apr. 23, 1998, now Pat. No. 6,007,484, which is a continuation of application No. 08/937,238, filed on Sep. 16, 1997, now Pat. No. 5,762,603, which is a continuation of application No. 08/708,044, filed on Aug. 30, 1996, now abandoned.
(60) Provisional application No. 60/003,802, filed on Sep. 15, 1995.

(51) Int. Cl.⁷ .................................................. A61B 1/05
(52) U.S. Cl. ...................... 600/173; 600/137; 600/109; 600/122; 348/82
(58) Field of Search ................................ 600/102, 103, 600/114, 122, 109, 137, 129, 160, 170–173, 121, 112; 348/82–85, 65, 143, 144, 155, 206

(56) References Cited

U.S. PATENT DOCUMENTS

| | | |
|---|---|---|
| 3,557,780 A | 1/1971 | Sato |
| 3,896,793 A | 7/1975 | Mitsui et al. |
| 3,958,080 A | 5/1976 | Schadler |
| 4,697,210 A | 9/1987 | Toyota et al. |
| 4,718,417 A | 1/1988 | Kittrell et al. |
| 4,727,859 A | 3/1988 | Lia |
| 4,741,326 A | 5/1988 | Sidall et al. |
| 4,791,479 A | 12/1988 | Ogiu et al. |
| 4,819,620 A | 4/1989 | Okutsu |
| 4,855,838 A | 8/1989 | Jones et al. |
| 4,858,001 A | 8/1989 | Milbank et al. |
| 4,895,138 A | 1/1990 | Yabe |
| 4,905,082 A | 2/1990 | Nishigaki et al. |
| 4,947,827 A | 8/1990 | Opie et al. |
| 4,971,035 A | 11/1990 | Ito |
| 4,989,586 A | 2/1991 | Furukawa |
| 5,028,997 A | 7/1991 | Elberbaum |
| 5,111,288 A | 5/1992 | Blackshear |
| 5,166,787 A | 11/1992 | Irion |
| 5,217,453 A | 6/1993 | Wilk |
| 5,237,984 A | 8/1993 | Williams, III et al. |
| 5,243,967 A | 9/1993 | Hibino |
| 5,251,613 A | 10/1993 | Adair .............................. 128/6 |
| 5,253,638 A | 10/1993 | Tamburrino et al. |
| 5,267,970 A | 12/1993 | Chin et al. .................. 604/175 |
| 5,271,381 A | 12/1993 | Ailinger et al. |
| 5,290,168 A | 3/1994 | Cooper et al. |
| 5,305,121 A | 4/1994 | Moll |
| 5,307,804 A | 5/1994 | Bonnet |
| 5,308,325 A | 5/1994 | Quinn et al. |
| 5,334,150 A | 8/1994 | Kaali |
| 5,349,941 A | 9/1994 | Hori |

(List continued on next page.)

FOREIGN PATENT DOCUMENTS

| | | |
|---|---|---|
| DE | 78 33 379 | 10/1978 |
| DE | 78 33 379 | 2/1979 |
| JP | 23 25 24 | 8/2000 |
| WO | 91 13080.8 | 1/1992 |
| WO | WO 96/10947 | 4/1996 |

*Primary Examiner*—John P. Leubecker
(74) *Attorney, Agent, or Firm*—Wolf, Greenfield & Sacks, P.C.

(57) ABSTRACT

A surgical/diagnostic imaging device for use in interabdominal, interthoracic, and other surgical and diagnostic procedures includes an image sensor pivotally mounted at the distal end of a support. In use, the image sensor and support are contained within a disposable sterile sheath, and the distal portion of the sheath is inserted into the patient through an incision. The imaging device includes actuators to move the image sensor in elevation and azimuth.

80 Claims, 5 Drawing Sheets

U.S. PATENT DOCUMENTS

| | | |
|---|---|---|
| 5,351,678 A | 10/1994 | Clayton et al. |
| 5,368,015 A | 11/1994 | Wilk |
| 5,380,291 A | 1/1995 | Kaali |
| 5,381,784 A | 1/1995 | Adair |
| 5,381,943 A | 1/1995 | Allen et al. |
| 5,383,859 A | 1/1995 | Sewell, Jr. .................. 604/164 |
| 5,396,879 A | 3/1995 | Wilk et al. |
| 5,402,768 A | 4/1995 | Adair |
| 5,418,567 A | 5/1995 | Boers et al. ................. 348/143 |
| 5,458,132 A | 10/1995 | Yabe et al. |
| 5,483,951 A | 1/1996 | Frassica et al. |
| 5,489,256 A | 2/1996 | Adair |
| 5,508,735 A | 4/1996 | Mueller |
| 5,531,664 A | 7/1996 | Adachi et al. |
| 5,538,497 A | 7/1996 | Hori |
| 5,540,649 A | 7/1996 | Bonnell et al. |
| 5,558,619 A | 9/1996 | Kami et al. |
| 5,562,602 A | 10/1996 | Yabe et al. |
| 5,573,494 A | 11/1996 | Yabe et al. |
| 5,591,192 A | 1/1997 | Privitera et al. |
| 5,617,762 A | 4/1997 | Kirsch ........................ 348/143 |
| 5,626,553 A | 5/1997 | Frassica et al. |
| 5,689,365 A | 11/1997 | Takahashi ................... 600/166 |
| 5,737,013 A | 4/1998 | Williams et al. |
| 5,762,603 A | 6/1998 | Thompson |
| 5,879,289 A | 3/1999 | Yarush et al. |
| 5,908,294 A | 6/1999 | Schick et al. |
| 6,007,484 A | 12/1999 | Thompson |

ENDOSCOPE HAVING ELEVATION AND AZIMUTH CONTROL OF CAMERA

This application is a divisional of application Ser. No. 09/065,116, filed Apr. 23, 1998, now U.S. Pat. No. 6,007,484, which is a continuation of application Ser. No. 08/937,238, filed Sep. 16, 1997, now U.S. Pat. No. 5,762,603, which is a continuation of application Ser. No. 08/708,044, filed Aug. 30, 1996, now abandoned, which claims the benefit of Provisional Application No. 60/003,802, filed Sep. 15, 1995.

TECHNICAL FIELD OF THE INVENTION

This invention is related to an imaging device for use in interabdominal, interthoracic, and other surgical and diagnostic procedures on the human body.

BACKGROUND

Endoscopic surgery and diagnosis are considerably less invasive than the conventional procedures. This results in a lower mortality rate and minimizes both the patient's hospital stay and recovery time.

Conventional endoscopes include a rigid elongated member, a lens assembly, and an imaging device mounted either on or within the endoscope. Examples of such endoscopes are described in U.S. Pat. No. 4,697,210 (Toyota et al.), U.S. Pat. No. 4,791,479 (Ogiu et al.), and U.S. Pat. No. 4,989,586 (Furukawa).

Although a conventional endoscope can be constructed to have a wide field of view, the picture quality suffers. As a practical matter, the field of view of conventional endoscopes must be relatively narrow. As a result, a conventional endoscope must be positioned carefully at the beginning of a procedure, then held in position throughout the procedure, which generally requires the full-time attention of one member of the operating team. U.S. Pat. No. 5,351,678 (Clayton et al.) addresses the initial positioning problem by providing an endoscope having a distal end which is offset from the endoscope's longitudinal axis. With the Clayton et al. endoscope, the surgeon can easily change the area viewed by rotating the endoscope about its longitudinal axis. However, the Clayton et al. endoscope must still be held in place throughout the procedure by a member of the operating team.

SUMMARY OF THE INVENTION

A surgical/diagnostic imaging device embodying the invention includes a charge-coupled device ("CCD") and an associated lens mounted within a camera bore in a camera housing. The camera housing is pivotally mounted at the distal end of an elongated camera support. High intensity lights are also mounted within bores in the camera housing that are coaxial with the camera bore and thus with the axis of the CCD.

Prior to use, the camera housing and camera support tube are inserted into a disposable sterile sheath. The distal portion of the sheath is then inserted into the patient through an incision in the patient. Electric stepper motors and associated components are provided to move the camera housing (and thus the CCD) in elevation and azimuth.

The imaging device is electrically connected to a control console. The control console is in turn electrically connected to a display device and a control assembly. The display device displays the image received by the CCD and the control assembly allows the surgeon to control the elevation and azimuth of the camera housing.

The surgical/diagnostic imaging device is easily aimed at the area of interest within the patient by the surgeon. In addition, surgical/diagnostic imaging device need not be held in position in the patient by a member of the operating team.

BRIEF DESCRIPTION OF THE DRAWINGS

An embodiment of the invention will be described, by way of example only, with reference to the accompanying drawings, in which.

DETAILED DESCRIPTION

Figures 1, 2, 3:
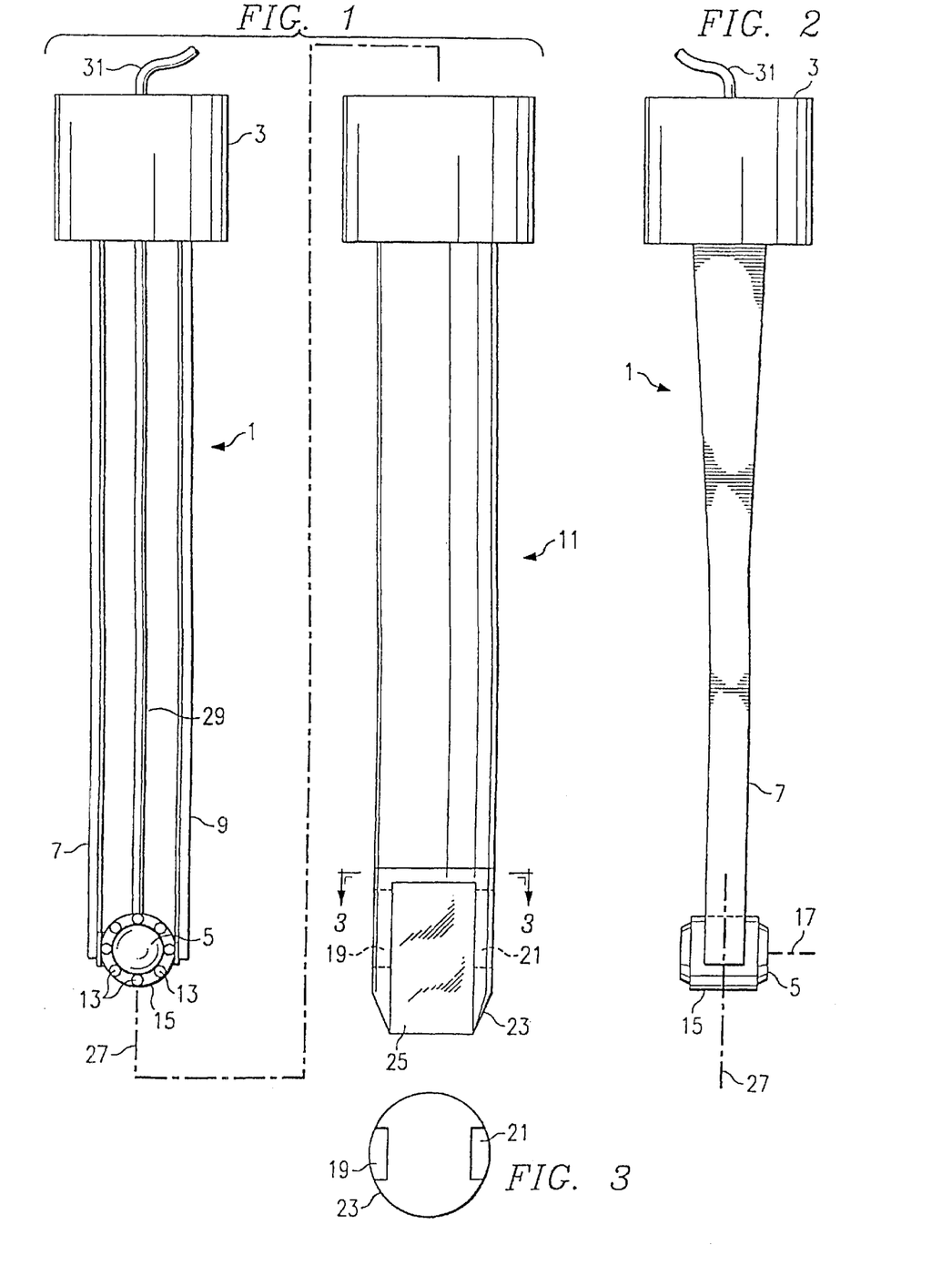
FIG. 1 is a front view of a surgical/diagnostic imaging device in accordance with the invention.
FIG. 2 is a partially cutaway side view of the imaging device of FIG. 1.
FIG. 3 is a cutaway top view of the sheath cap taken through plane 3—3 in FIG. 1.

FIGS. 1–3 show a surgical/diagnostic imaging device 1 for use in interabdominal, interthoracic, and other surgical and diagnostic procedures. The device 1 comprises an upper housing 3, a camera housing 5, and left and right camera housing supports 7, 9. Before use, the device 1 is inserted into a sterile sheath 11. The device 1 and sheath 11 (collectively, the "camera") are then inserted through an incision (not shown) into the patient's body (not shown). The camera is inserted so as place the camera housing 5 in a position from which it can be pointed at the surgical site or the area to be diagnosed. The incision is sealed around the camera with a purse string stitch, thereby preventing leakage of the $CO_2$ gas which is used to distend the patient's abdomen or chest during surgery or diagnosis.

In this embodiment, the sheath 11 is constructed of medical-grade plastic is provided in a sterilized condition and is intended to be disposed of after use. Alternately, the sheath 11 can be constructed of heat-resistant materials in order to allow it to be sterilized using an autoclave, then reused should be appreciated that the sterile sheath.

The camera housing 5 contains a CCD (not shown) and a zoom lens assembly (not shown). A plurality of high intensity lights 13 are mounted within a light housing 15 which extends about the outer circumference of the camera housing 5. The lights 13 are aligned with the focal axis 17 of the CCD, and they provide illumination of the area at which the camera housing 5 and hence the CCD are pointed.

When the device 1 is inserted in the sheath 11, the left and right camera housing supports 7, 9 engage complimentary locking keys 19, 21 within a sheath cap 23. As a result, the camera housing 5 is locked into a position in which the CCD's focal axis 17 is aligned perpendicular to an optically-clear window 25. In addition, as will be described below in connection with FIGS. 4–6, the locking keys 19, 21 cause the sheath cap 13 to rotate about the longitudinal axis 27 of the camera when the camera housing supports 7, 9 are rotated about that axis.

A camera cable 29 extends between the camera housing 5 and the upper housing 3. The camera cable 29 contains conductors which carry the CCD's signals to the upper housing 3 and which supply electrical power to the CCD and lights 13. An imaging device cable 31 is provided to carry control signals and supply electrical power to the device 1 and to carry the CCD's signals to external processing and display devices (not shown).

The length of the camera housing supports 7, 9 and the length of the sheath 11 are varied to accommodate variation in the thickness of the abdominal walls of patients and to allow the camera to be used in thoracic surgery/diagnosis. Three lengths are provided: 3, 6, and 11 inches below the upper housing 3.

Figure 4:
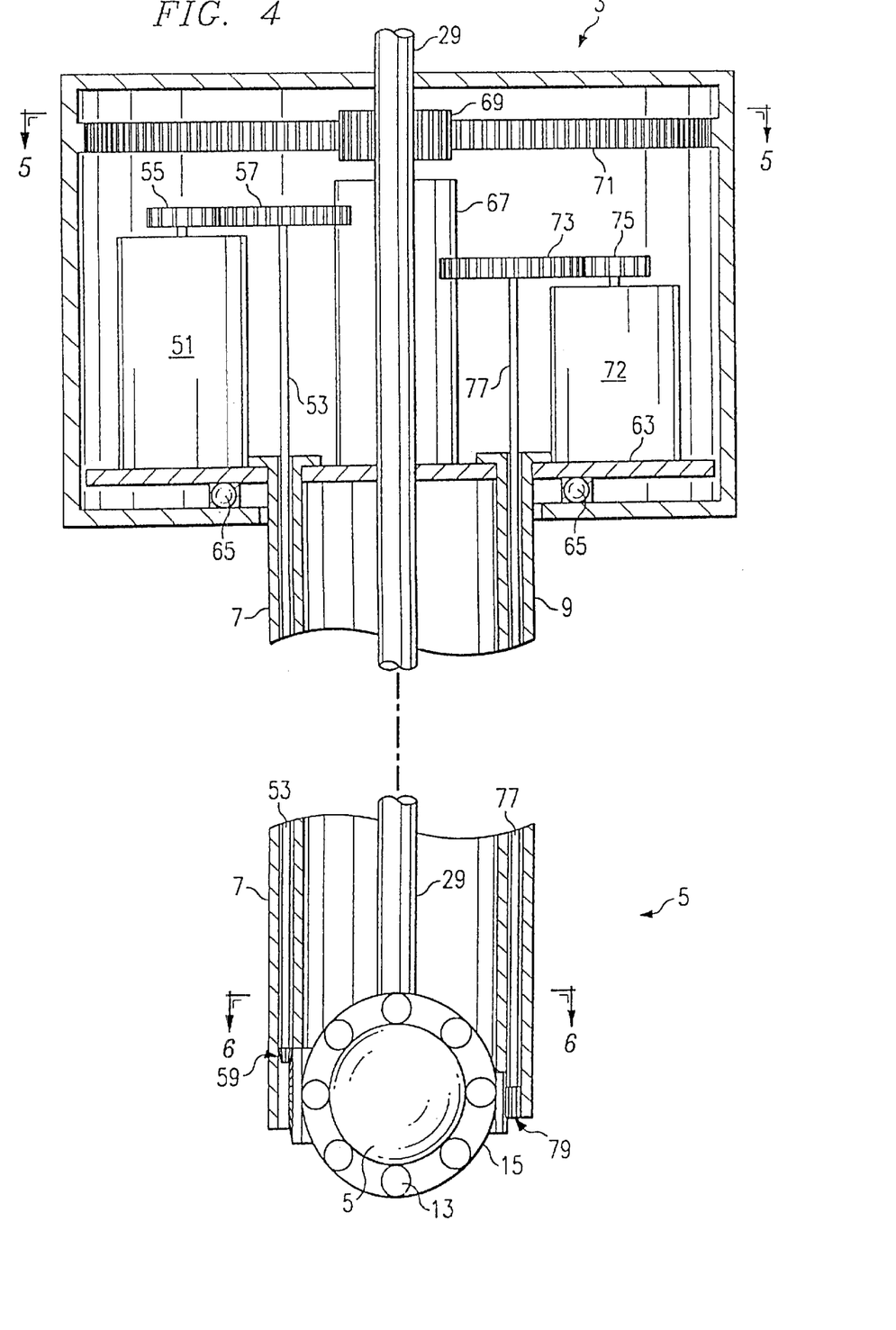
FIG. 4 is an enlarged cutaway side view of the upper housing and the lower portion of the imaging device.
Figure 5:
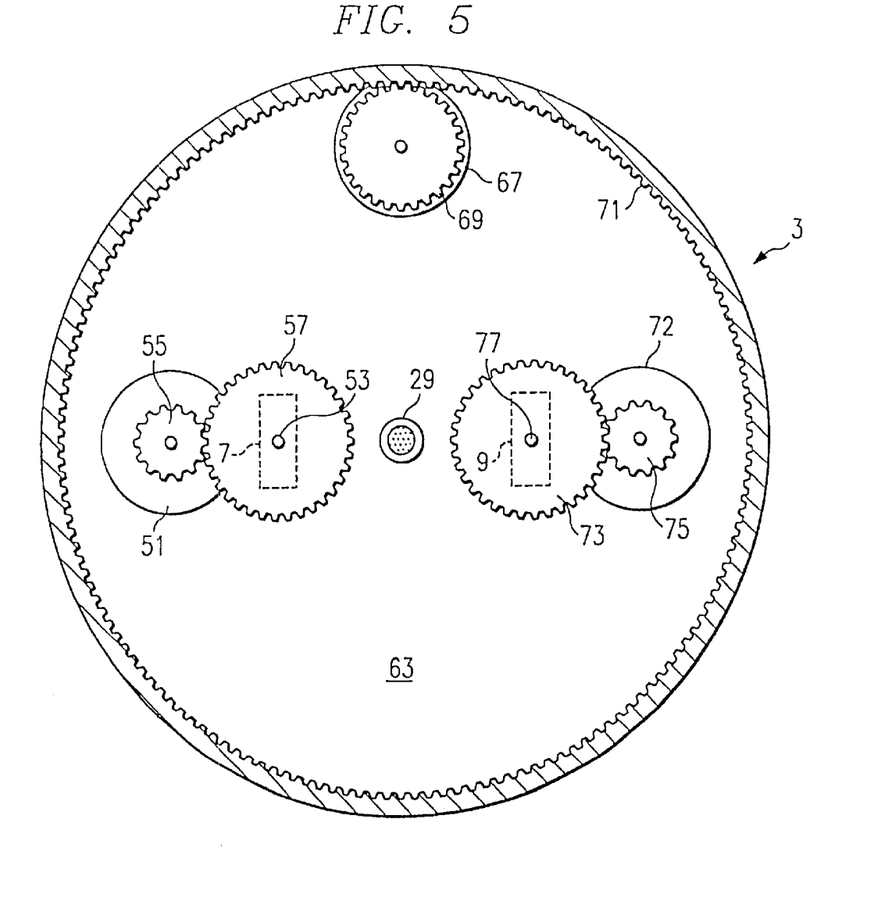
FIG. 5 is a cutaway top view of the upper housing taken through plane 5—5 in FIG. 4.
Figure 6:
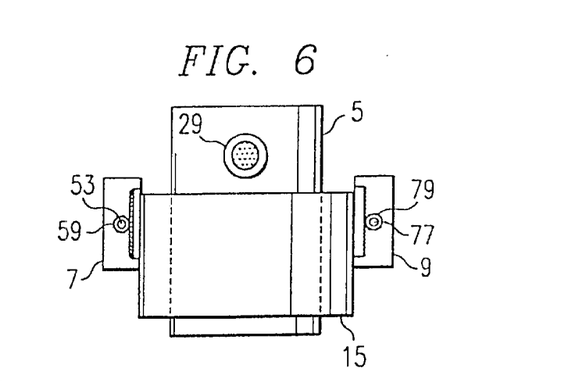
FIG. 6 is an cutaway top view of the lower portion of the imaging device taken through plane 6—6 in FIG. 4.

Referring now to FIGS. 4–6, an elevation motor 51 drives an elevation shaft 53 by means of gears 55, 57. The elevation shaft 53 extends downwardly through the hollow left camera support 7. A ring and pinon gear arrangement 59 at the lower end of the elevation shaft 53 transfers the rotary motion of the elevation shaft 53 to the camera housing 15, thereby causing the camera housing 15 to elevate or depress, depending on the direction of rotation of the elevation motor 51. In this embodiment of the invention, the camera housing 15 can be elevated 70 degrees above and depressed 90 degrees below above a plane perpendicular to the longitudinal axis 27 of the camera and passing through intersection of the longitudinal axis 27 and the focal axis 17 of the camera.

The elevation motor 51 is mounted on a plate 63. The plate 63 is rotably mounted within the upper housing 3 on a bearing 65.

An azimuth motor 67 is also mounted on the plate 63. The azimuth motor 67 drives an azimuth gear 69. The azimuth gear 69 engages a housing gear 71 which is attached to the inner surface of the upper housing 3. When the azimuth motor 67 rotates, the plate 63 rotates within the upper housing 3. In this embodiment, the plate 63 rotates plus or minus 180 degrees in order to minimize the amount the camera cable 21 is twisted. 360 degree rotation can easily be achieved by using conventional slip rings.

A zoom/focus motor 72 drives gears 73, 75, which rotate a zoom/focus shaft 77. The zoom/focus shaft extends downwardly through the right camera support 9. At the bottom of the focus shaft 77, a ring and pinon arrangement 79 transfers the rotary motion of the focus shaft 77 to a zoom lens mechanism (not shown) within the camera housing 5.

Figure 7:
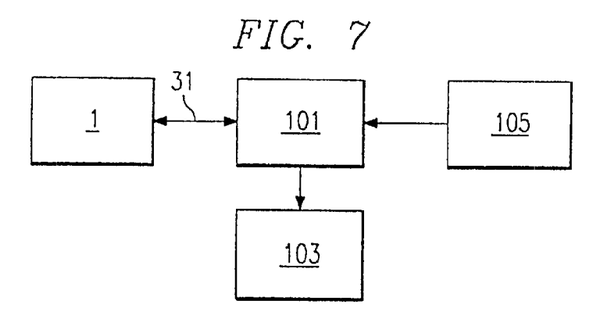
FIG. 7 is a block diagram of a system for controlling the imaging device of FIG. 1 and for displaying the images transmitted by the imaging device.

Referring now to FIG. 7, the imaging device 1 is connected to a control console 101 by means of the imaging device cable 31. signals from the CCD of the imaging device 1 are amplified by circuits in the control console 101 and directed to a display device 103. In this embodiment of the invention, the display device 103 is a conventional television set.

A foot pedal control assembly 105 allows the surgeon (not shown) to control the imaging device 1. The foot pedal control assembly 105 includes four controls (not shown): (1) camera 10 housing left and right; (2) camera housing up and down; (3) zoom in and out; and (4) light intensity up and down. Signals from the foot pedal control assembly 105 are routed to the control console 101. Circuits (not shown) in the control console 103 convert the control assembly signals into signals which are suitable to control the imaging device 1, then route the converted signals to the imaging device 1.

Figure 8:
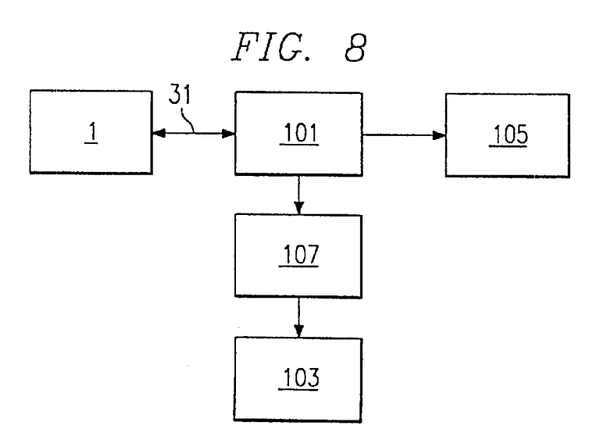
FIG. 8 is a block diagram of a second control and display system for the imaging device of FIG. 1.

In the embodiment of the invention shown in FIG. 8, a computer 107 is interposed between the control console 101 and the display device 103. A plurality of computer programs contained in the computer 107 allow operating team personnel to manipulate and/or store the signals from the imaging device 1.

Figure 9:
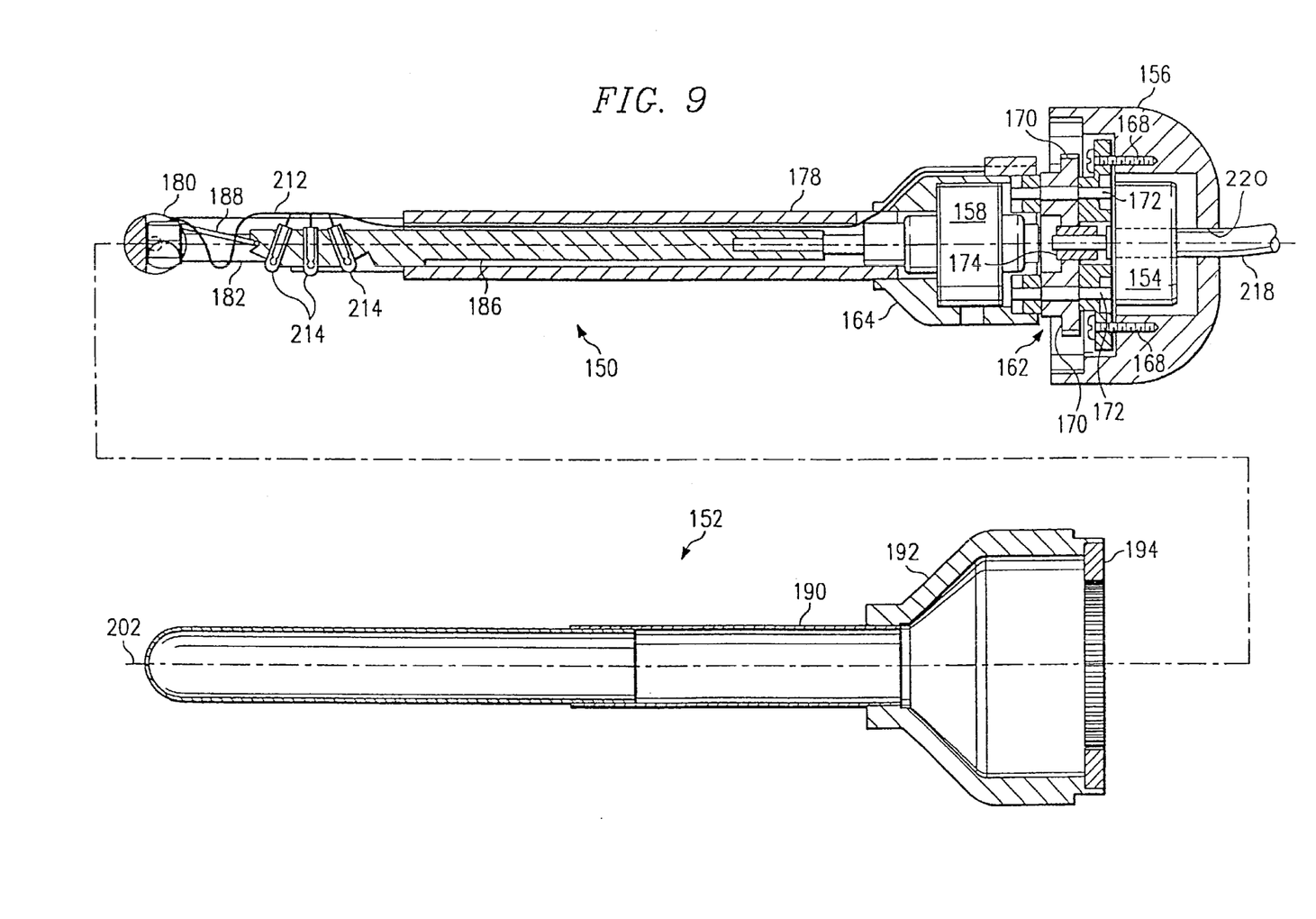
FIG. 9 is a cutaway side view of a second imaging device in accordance with the invention.
Figure 10:
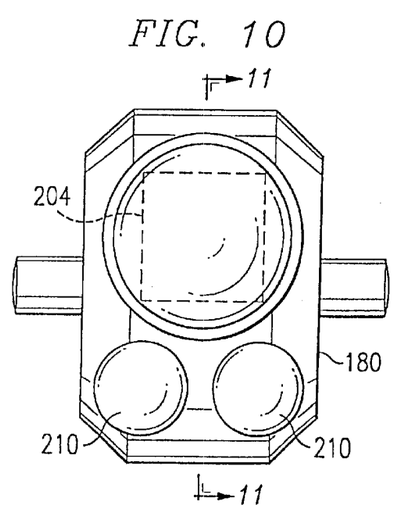
FIG. 10 is a front view of the camera housing shown in FIG. 10.
Figure 11:
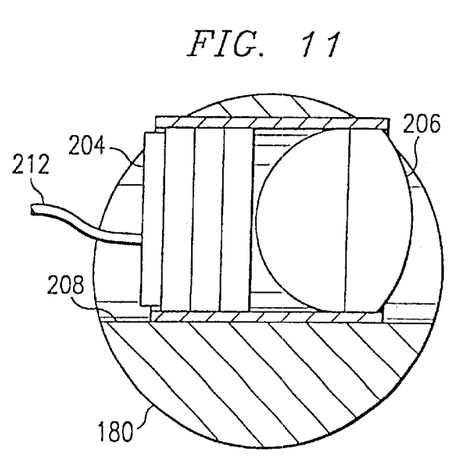
FIG. 11 is a cutaway side view of the camera housing taken through plane 11—11 in FIG. 10.

FIGS. 9–11 illustrate a second surgical/diagnostic imaging device in accordance with the invention. Referring first to FIG. 9, the imaging device comprises two major assemblies: a camera assembly 150 and a disposable sheath assembly 152.

In the camera assembly 150, a rotary stepper motor 154 is rigidly mounted in an upper housing 156. A linear stepper motor 158 and the distal end of a planetary gear assembly 162 are press fitted in a linear stepper motor housing 164. The proximal end of the planetary gear assembly 162 is attached to the upper housing 156 by screws 168.

Three planetary gears 170 (only two of which are shown in FIG. 9) are rotably mounted on pins 172 within the planetary gear assembly 162. The rotary stepper motor 154 drives the planetary gears 170 through a sun gear 174.

The proximal end of a camera support tube 178 is press fitted in the linear stepper housing 164. A camera housing 180 is pivotally mounted between pair of arms 182 (only one of which is shown in FIG. 9) that are integral with and extend from the distal end of the camera support tube 178. The linear stepper motor 158 acts through a pushrod 186 and a fork 188 to control the elevation of the camera housing 180.

The disposable sheath assembly 152 comprises a sheath 190, a sheath housing 192, and a ring gear 194. The distal portion of the sheath 190 is optically clear. The proximal end of the sheath 190 is adhesively attached within the distal end of the sheath housing 192. The ring gear 194 is adhesively attached within the proximal end of the sheath housing 192.

Prior to use, the camera assembly 150 is inserted into the sheath assembly 152, and the planet gears 170 engage the ring gear. As a result, when the rotary stepper motor 154 is actuated, the camera assembly 150 rotates in relation to the longitudinal axis 202 of the sheath assembly As is best shown in FIGS. 10 and 11, a CCD assembly 204 and a lens 206 are mounted within a camera bore 208 in the camera housing 180. A pair of high intensity lights 210 are mounted in bores that are coaxial with the camera bore 208.

A multi-conductor flexcable 212 provides the necessary connections for the CCD assembly 204, for the camera housing lights 210, and for three high intensity lights 214 that are disposed in bores in the pushrod 186. The flexcable 212 extends from the camera housing 180 to the upper housing 156. In the upper housing 156, the flexcable 212 is combined with power and control wires (not shown) for the rotary stepper motor 154 and the linear stepper motor 158 to form the camera assembly cable 218. The camera assembly cable 218 passes through an orifice 220 in the upper housing 152. As with the embodiment of the invention shown in FIGS. 1–8, the camera assembly cable 218 connects the camera assembly 150 to external display and control devices (not shown).

What is claimed is:

1. An image-sensing apparatus, comprising:
   a sheath having a proximal end, a distal end opposite the proximal end, and an optically-clear section;

an image sensor, having an imaging axis, disposed within the sheath adjacent the distal end of the sheath and the optically-clear section of the sheath such that the imaging axis can intersect the optically-clear section of the sheath; and a support member, having a proximal end, a distal end opposite the proximal end, and a longitudinal axis extending between the proximal and distal ends of the support member, supporting the image sensor within the sheath, the image sensor being pivotally coupled to the support member adjacent the distal end of the support member such that the image sensor can pivot about a pivot axis and such that the imaging axis can be oriented at commonly-measured angles that are both greater than and less than ninety degrees with respect to the longitudinal axis, the support member being at least partially disposed within the sheath and being rotatable relative to at least the optically-clear section of the sheath, at least a portion of the optically-clear section of the sheath being disposed both proximally and distally of the pivot axis such that the imaging axis intercepts the optically-clear section of the sheath when the imaging axis is oriented at the commonly-measured angles that are both greater than and less than ninety degrees with respect to the longitudinal axis.

2. The image-sensing apparatus as claimed in claim 1, wherein the support member is spaced from the optically-clear section of the sheath throughout its range of motion.

3. The image-sensing apparatus as claimed in claim 1, wherein the image sensor is supported by the support member so that the imaging axis of the image sensor can pivot through a pivoting range about the pivot axis, the pivot axis maintaining a constant relationship with respect to the support member throughout the pivoting range of the imaging axis.

4. The image-sensing apparatus as claimed in claim 3, wherein the image sensor is supported by the support member so that the imaging axis of the image sensor pivots about only one pivot axis.

5. The image-sensing apparatus as claimed in claim 3, further comprising a camera housing, supporting the image sensor, pivotally connected to the support member.

6. The image-sensing apparatus as claimed in claim 1, further comprising an elevation driver arranged to move the image sensor to adjust an elevation of the imaging axis relative to the longitudinal axis of the support member.

7. The image-sensing apparatus as claimed in claim 6, wherein:

the image sensor is supported by the support member near the distal end of the support member, and the elevation driver is located near the proximal end of the support member.

8. The image-sensing apparatus as claimed in claim 1, further comprising an azimuth driver arranged to rotate the support member relative to at least the optically-clear section of the sheath.

9. The image-sensing apparatus as claimed in claim 8, wherein:

the image sensor is supported by the support member near the distal end of the support member, and the azimuth driver is located near the proximal end of the support member.

10. The image-sensing apparatus as claimed in claim 1, wherein the image sensor includes a charge coupled device.

11. The image-sensing apparatus as claimed in claim 1, wherein the support member is rigid.

12. The image-sensing apparatus as claimed in claim 11, wherein the sheath is rigid.

13. The image-sensing apparatus as claimed in claim 1, wherein the sheath is rigid.

14. The image-sensing apparatus of claim 1, further comprising at least one light source disposed within the sheath to illuminate the viewing area outside the sheath, the at least one light source converting energy from a non-light energy source into light.

15. The image-sensing apparatus as claimed in claim 1, wherein the image sensor is the only active electronic component mechanically coupled to the support member adjacent the distal end of the support member so that no other active electronics components move with the image sensor when the image sensor moves relative to the longitudinal axis.

16. An image-sensing apparatus, comprising:

sheath having a proximal end, a distal end opposite the proximal end, and an optically-clear section;

an image sensor, having an imaging axis, disposed within the sheath adjacent the distal end of the sheath and the optically-clear section of the sheath such that the imaging axis can intersect the optically-clear section of the sheath;

a support member having a proximal end, a distal end opposite the proximal end, and a longitudinal axis extending between the proximal and distal ends of the support member, the image sensor being movably coupled to the support member adjacent the distal end of the support member and the support member supporting the image sensor with respect to the sheath such that the image sensor can be moved, relative to at least the optically-clear section of the sheath, about at least two axes of rotation, and such that the image sensor can be moved about one of the at least two axes of rotation so as to orient the imaging axis at commonly-measured angles that are both greater than and less than ninety degrees with respect to the longitudinal axis, at least a portion of the optically-clear section of the sheath being disposed both proximally and distally of the one of the at least two axes of rotation such that the imaging axis intercepts the optically-clear section of the sheath when the imaging axis is oriented at the commonly-measured angles that are both greater than and less than ninety degrees with respect to the longitudinal axis; and at least one mechanical driver, located near the proximal end of the support member, to move the image sensor about at least one of the at least two axes of rotation.

17. The image-sensing apparatus as claimed in claim 16, wherein:

the at least one mechanical driver includes an azimuth driver and an elevation driver, the at least two axes of rotation include an azimuth axis and an elevation axis, the azimuth driver is arranged to rotate the image sensor about the azimuth axis, and the elevation driver is arranged to rotate the image sensor about the elevation axis.

18. The image-sensing apparatus as claimed in claim 16, further comprising a controller to control the at least one mechanical driver.

19. The image-sensing apparatus as claimed in claim 16, wherein at least a portion of the support member is disposed within the sheath.

20. The image-sensing apparatus as claimed in claim 16, wherein the image sensor includes a charge coupled device.

21. The image-sensing apparatus as claimed in claim 18, wherein the support member is rigid.

22. The image-sensing apparatus as claimed in claim 21, wherein the sheath is rigid.

23. The image-sensing apparatus as claimed in claim 16, wherein the sheath is rigid.

24. The image-sensing apparatus of claim 16, further comprising at least one light source disposed within the sheath to illuminate the viewing area outside the sheath, the at least one light source converting energy from a non-light energy source into light.

25. The image-sensing apparatus as claimed in claim 16, wherein the image sensor is the only active electronic component mechanically coupled to the support member adjacent the distal end of the support member so that no other active electronics components move with the image sensor when the image sensor moves relative to the longitudinal axis.

26. The image sensor of claim 25, wherein no electronic components other than the image sensor are disposed adjacent the distal end of the support member.

27. An image-sensing apparatus, comprising:
a sheath having a proximal end, a distal end opposite the proximal end, and an optically-clear section;
an image sensor, having an imaging axis, disposed within the sheath adjacent the distal end of the sheath and the optically-clear section of the sheath such that the imaging axis can intersect the optically-clear section of the sheath;
a support member having a proximal end, a distal end opposite the proximal end, and a longitudinal axis extending between the proximal and distal ends of the support member, the image sensor being movably coupled to the support member adjacent the distal end of the support member and the support member supporting the image sensor with respect to the sheath such that the image sensor can be moved, relative to at least the optically-clear section of the sheath, about at least two axes of rotation, and such that the image sensor can be pivoted about one of the at least two axes of rotation so as to orient the imaging axis at commonly-measured angles that are both greater than and less than ninety degrees with respect to the longitudinal axis, at least a portion of the optically-clear section of the sheath being disposed both proximally and distally of the one of the at least two axes of rotation such that the imaging axis intercepts the optically-clear section of the sheath when the imaging axis is oriented at the commonly-measured angles that are both greater than and less than ninety degrees with respect to the longitudinal axis; and
at least one linkage arranged to transfer physical forces from the proximal end of the support member to the distal end of the support member so as to control movement of the image sensor about at least one of the at least two axes of rotation.

28. The image-sensing apparatus as claimed in claim 27, wherein:
the at least one linkage includes an azimuth linkage and an elevation linkage,
the at least two axes of rotation include an azimuth axis and an elevation axis, the azimuth linkage is arranged to rotate the image sensor about the azimuth axis, and the elevation linkage is arranged to rotate the image sensor about the elevation axis.

29. The image-sensing apparatus as claimed in claim 27, wherein at least a portion of the support member is disposed within the sheath.

30. The image-sensing apparatus as claimed in claim 27, wherein the image sensor includes a charge coupled device.

31. The image-sensing apparatus as claimed in claim 27, wherein the support member is rigid.

32. The image-sensing apparatus as claimed in claim 31, wherein the sheath is rigid.

33. The image-sensing apparatus as claimed in claim 27, wherein the sheath is rigid.

34. The image-sensing apparatus of claim 27, further comprising at least one light source disposed within the sheath to illuminate the viewing area outside the sheath, the at least one light source converting energy from a non-light energy source into light.

35. The image-sensing apparatus as claimed in claim 27, wherein the image sensor is the only active electronic component mechanically coupled to the support member adjacent the distal end of the support member so that no other active electronics components move with the image sensor when the image sensor moves relative to the longitudinal axis.

36. The image sensor of claim 35, wherein no electronic components other than the image sensor are disposed adjacent the distal end of the support member.

37. An image-sensing device, comprising:
a sheath having a proximal end, a distal end, an optically-clear section, and a longitudinal axis extending between the proximal and distal ends of the sheath;
an image sensor, having an imaging axis, disposed within the sheath adjacent the distal end of the sheath such that the imaging axis intersects the optically-clear section of the sheath; and
a rigid support member, which is movable relative to at least the optically-clear section of the sheath, at least partially disposed within the sheath and extending along the longitudinal axis of the sheath, the image sensor being movably coupled to the support member so that an imaging axis of the image sensor can pivot through a pivoting range about a pivot axis, the pivoting range including angular positions of the imaging axis that are both greater than and less than ninety degrees with respect to the longitudinal axis of the sheath, the pivot axis being disposed distally of at least a portion of the optically-clear section so that the imaging axis intercepts the optically-clear section of the sheath when the imaging axis is oriented at the angular positions of the imaging axis that are both greater than and less than ninety degrees with respect to the longitudinal axis of the sheath, the pivot axis maintaining a constant relationship with respect to the support member throughout the pivoting range of the imaging axis.

38. The image-sensing apparatus as claimed in claim 37, wherein the image sensor is supported by the support member so that the imaging axis of the image sensor pivots about only one pivot axis.

39. The image-sensing apparatus as claimed in claim 37, further comprising a camera housing, supporting the image sensor, pivotally connected to the support member along the pivot axis.

40. The image-sensing apparatus as claimed in claim 37, wherein the image sensor includes a charge coupled device.

41. The image-sensing apparatus of claim 37, further comprising at least one light source disposed within the sheath to illuminate the viewing area outside the sheath, the at least one light source converting energy from a non-light energy source into light.

42. The image-sensing apparatus as claimed in claim 37, wherein the image sensor is the only active electronic component mechanically coupled to the support member adjacent the distal end of the support member so that no other active electronics components move with the image sensor when the image sensor moves relative to the longitudinal axis.

43. The image sensor of claim 37, wherein no electronic components other than the image sensor are disposed adjacent the distal end of the support member.

44. An image-sensing apparatus, comprising:
   a base;
   a support member, having a proximal end, a distal end, and a longitudinal axis extending between the proximal and distal ends, the proximal end of the support member being rotatably coupled to the base;
   an optically-clear window supported by the base; and
   an image sensor, having an imaging axis, movably coupled to the support member adjacent the distal end of the support member such that the imaging axis can pivot through a range of angles with respect to the longitudinal axis, including commonly-measured angles that are both greater than and less than ninety degrees with respect to the longitudinal axis, the optically-clear window being configured and arranged with respect to the image sensor such that the imaging axis intercepts different portions of the optically-clear window as the imaging axis pivots through the range of angles, including the commonly-measured angles that are greater than and less than ninety degrees with respect to the longitudinal axis.

45. The image-sensing apparatus of claim 44, wherein the optically-clear window is supported by the base such that the support member can rotate, about the longitudinal axis, with respect to both the base and the optically-clear section.

46. The image-sensing apparatus as claimed in claim 44, wherein the support member and image sensor are spaced from the optically-clear window throughout their ranges of motion.

47. The image-sensing apparatus as claimed in claim 44, wherein the image sensor is supported by the support member so that the imaging axis of the image sensor can pivot through a pivoting range about a pivot axis, the pivot axis maintaining a constant relationship with respect to the support member throughout the pivoting range of the imaging axis.

48. The image-sensing apparatus as claimed in claim 47, wherein the image sensor is supported by the support member so that the imaging axis of the image sensor pivots about only one pivot axis.

49. The image-sensing apparatus as claimed in claim 44, further comprising a camera housing, supporting the image sensor, pivotally connected to the support member.

50. The image-sensing apparatus as claimed in claim 44, wherein the base comprises a housing, and wherein the image sensing apparatus further comprises an elevation driver, disposed within the housing, configured and arranged to move the image sensor to adjust an elevation of the imaging axis relative to the longitudinal axis of the support member.

51. The image-sensing apparatus as claimed in claim 50, further comprising an azimuth driver, disposed within the housing, arranged to rotate the support member relative to the housing.

52. The image-sensing apparatus as claimed in claim 44, wherein the base comprises a housing, and wherein the image sensing apparatus further comprises an azimuth driver, disposed within the housing, configured and arranged to rotate the support member relative to the housing.

53. The image-sensing apparatus as claimed in claim 44, wherein the image sensor includes a charge coupled device.

54. The image-sensing apparatus as claimed in claim 44, wherein the support member is rigid.

55. An image-sensing apparatus, comprising:
   a base;
   a support member, having a proximal end, a distal end, and a longitudinal axis extending between the proximal and distal ends, the proximal end of the support member being rotatably coupled to the base; and
   an image sensor, having an imaging axis, movably coupled to the support member adjacent the distal end of the support member such that the imaging axis can pivot through a range of angles with respect to the longitudinal axis, including commonly-measured angles that are both greater than and less than ninety degrees with respect to the longitudinal axis, the image sensor producing a signal in response to light being reflected by an object;
      wherein the image sensor is the only active electronic component movably coupled to the support member adjacent the distal end of the support member so that no other active electronics components move with the image sensor when the image sensor moves relative to the longitudinal axis.

56. The image sensor of claim 55, wherein no electronic components other than the image sensor are disposed at the distal end of the support member so as to move with the image sensor when the image sensor moves with respect to the distal end of the support member.

57. The image-sensing apparatus as claimed in claim 55, wherein the image sensor is supported by the support member so that the imaging axis of the image sensor can pivot through a pivoting range about a pivot axis, the pivot axis maintaining a constant relationship with respect to the support member throughout the pivoting range of the imaging axis.

58. The image-sensing apparatus as claimed in claim 57, wherein the image sensor is supported by the support member so that the imaging axis of the image sensor pivots about only one pivot axis.

59. The image-sensing apparatus as claimed in claim 55, further comprising a camera housing, supporting the image sensor, pivotally connected to the support member.

60. The image-sensing apparatus as claimed in claim 55, wherein the base comprises a housing, and wherein the image sensing apparatus further comprises an elevation driver, disposed within the housing, configured and arranged to move the image sensor to adjust an elevation of the imaging axis relative to the longitudinal axis of the support member.

61. The image-sensing apparatus as claimed in claim 60, further comprising an azimuth driver, disposed within the housing, arranged to rotate the support member relative to the housing.

62. The image-sensing apparatus as claimed in claim 55, wherein the base comprises a housing, and wherein the image sensing apparatus further comprises an azimuth driver, disposed within the housing, configured and arranged to rotate the support member relative to the housing.

63. The image-sensing apparatus as claimed in claim 55, wherein the image sensor includes a charge coupled device.

64. The image-sensing apparatus as claimed in claim 55, wherein the support member is rigid.

65. An image-sensing apparatus, comprising:
   a base;
   an image sensor having an imaging axis;
   a support member having a proximal end, a distal end opposite the proximal end, and a longitudinal axis extending between the proximal and distal ends of the support member, the image sensor being mechanically coupled to the support member adjacent the distal end of the support member and the support member being mechanically coupled to the base such that the image sensor can be moved about at least two axes of rotation; and at least one mechanical driver, located near the proximal end of the support member, to move the image sensor about each of the at least two axes of rotation;

wherein the image sensor is the only active electronic component mechanically coupled to the support member adjacent the distal end of the support member so that no other active electronics components move with the image sensor when the image sensor moves relative to the longitudinal axis.

66. The image sensor of claim 65, wherein no electronic components other than the image sensor are disposed adjacent the distal end of the support member so as to move with the image sensor when the image sensor moves with respect to the distal end of the support member.

67. The image-sensing apparatus as claimed in claim 65, wherein:

the at least one mechanical driver includes an azimuth driver and an elevation driver, the at least two axes of rotation include an azimuth axis and an elevation axis, the azimuth driver is arranged to rotate the image sensor about the azimuth axis, and the elevation driver is arranged to rotate the image sensor about the elevation axis.

68. The image-sensing apparatus as claimed in claim 65, further comprising a controller to control the at least one mechanical driver.

69. The image-sensing apparatus as claimed in claim 65, wherein the image sensor includes a charge coupled device.

70. The image sensor of claim 65, wherein no electronic components other than the image sensor are disposed adjacent the distal end of the support member.

71. An image-sensing apparatus, comprising:

a base;

an image sensor having an imaging axis;

a support member having a proximal end, a distal end opposite the proximal end, and a longitudinal axis extending between the proximal and distal ends of the support member, the image sensor being mechanically coupled to the support member adjacent the distal end of the support member and the support member being mechanically coupled to the base such that the image sensor can be moved about at least two axes of rotation; and at least one linkage arranged to transfer physical forces from the proximal end of the support member to the distal end of the support member so as to control movement of the image sensor about each of the at least two axes of rotation;

wherein the image sensor is the only active electronic component mechanically coupled to the support member adjacent the distal end of the support member so that no other active electronics components move with the image sensor when the image sensor moves relative to the longitudinal axis.

72. The image-sensing apparatus as claimed in claim 71, wherein:

the at least one linkage includes an azimuth linkage and an elevation linkage, the at least two axes of rotation include an azimuth axis and an elevation axis, the azimuth linkage is arranged to rotate the image sensor about the azimuth axis, and the elevation linkage is arranged to rotate the image sensor about the elevation axis.

73. The image-sensing apparatus as claimed in claim 71, wherein the image sensor includes a charge coupled device.

74. An image-sensing apparatus, comprising:

a base;

an image sensor having an imaging axis;

a support member having a proximal end, a distal end opposite the proximal end, and a longitudinal axis extending between the proximal and distal ends of the support member, the image sensor being mechanically coupled to the support member adjacent the distal end of the support member and the support member being mechanically coupled to the base such that the image sensor can be moved about at least two axes of rotation, and such that the image sensor can be pivoted about one of the at least two axes of rotation so as to orient the imaging axis at commonly-measured angles that are both greater than and less than ninety degrees with respect to the longitudinal axis; and at least one mechanical driver, located near the proximal end of the support member, to move the image sensor about each of the at least two axes of rotation.

75. The image-sensing apparatus of claim 74, wherein the proximal end of the support member is rotatably coupled to the base.

76. The image-sensing apparatus of claim 75, wherein the image sensor is pivotally coupled to the support member adjacent the distal end of the support member.

77. The image-sensing apparatus of claim 74, wherein the image sensor is pivotally coupled to the support member adjacent the distal end of the support member.

78. The image-sensing apparatus as claimed in claim 74, wherein:

the at least one mechanical driver includes an azimuth driver and an elevation driver, the at least two axes of rotation include an azimuth axis and an elevation axis, the azimuth driver is arranged to rotate the image sensor about the azimuth axis, and the elevation driver is arranged to rotate the image sensor about the elevation axis.

79. The image-sensing apparatus as claimed in claim 74, further comprising a controller to control the at least one mechanical driver.

80. The image-sensing apparatus as claimed in claim 74, wherein the image sensor includes a charge coupled device.

* * * * *